United States Patent [19]

Walsh

[11] 4,018,892
[45] Apr. 19, 1977

[54] BONE DEPOSITION BY 16-ARYL-13,14-DIHYDRO-PGE$_2$ P-BIPHENYL ESTERS

[75] Inventor: Alexander H. Walsh, Old Saybrook, Conn.

[73] Assignee: Pfizer Inc., New York, N.Y.

[22] Filed: Mar. 31, 1976

[21] Appl. No.: 672,449

Related U.S. Application Data

[62] Division of Ser. No. 602,478, Aug. 6, 1975, Pat. No. 3,982,016.

[52] U.S. Cl. .............................................. 424/285
[51] Int. Cl.$^2$ ....................................... A61K 31/34
[58] Field of Search ................................... 424/285

[56] References Cited

OTHER PUBLICATIONS

Chem. Abst. General Subject Index – vol. 83 July–Dec. 1975, p. 1583GS.

*Primary Examiner*—Sam Rosen
*Attorney, Agent, or Firm*—Connolly and Hutz

[57] ABSTRACT

Bone deposition in animals is produced by the administration of a 16-aryl-13,14-dihydro-PGE$_2$ p-biphenyl ester.

1 Claim, No Drawings

BONE DEPOSITION BY 16-ARYL-13,14-DIHYDRO-PGE$_2$ P-BIPHENYL ESTERS

This application is a division of application Ser. No. 602,478, filed Aug. 6, 1975, now U.S. Pat. No. 3,982,016.

BACKGROUND OF THE INVENTION

The term osteopenia is applied to a group of disorders characterized by a generalized loss of bone. These disorders include osteoporosis, osteomalacia, osteitis fibrosa cystica and bone loss associated with various malignancies, particularly multiple myeloma.

Osteoporosis, the most prevalent of the bone loss disorders, is a term applied to a heterogeneous group having in common a decreased skeletal mass that is usually associated with bone pain, vertebral compression, and an increased incidence of fractures in certain sites of predilection in the long bones, particularly the femoral neck, upper humerus, and distal radius and ulna. Treatment with estrogens, anabolic hormones, calcium and fluoride is directed toward increased bone deposition and the prevention of bone resorption.

SUMMARY OF THE INVENTION

This invention is concerned with a method for the treatment of osteopenia in animals which comprises administering to said animals a bone deposition increasing amount of a 16-aryl-13,14-dihydro-PGE$_2$ p-biphenyl ester.

DETAILED DESCRIPTION OF THE INVENTION

As used throughout the specification and claims, the term aryl denotes an organic radical derived from an aromatic hydrocarbon by the removal of one hydrogen atom such as phenyl, furyl, thienyl, naphthyl and the like. The term substituted phenyl refers to substituents in the ring by functional groups such as halogen, lower alkoxy and the like.

A 16-aryl-13,14-dihydro-PGE$_2$ p-biphenyl ester may be administered to a subject afflicted with bone loss via the oral or parenteral routes of administration. Variations in dosage may be made to achieve effective results which may depend on the subject being treated and individual response to the medicament, the weight of the subject as well as the particular type of compound formulation chosen and the time period and intervals at which such administration is conducted. In general it will be found that a bone deposition increasing amount of the esters of this invention ranges from about 0.1 to 0.45 mg/kg/day. These amounts may be administered in single or multiple doses. In some instances, dosage levels below the lower limit of the aforesaid range may be more than adequate while in other cases still larger doses may be employed without causing any harmful or deleterious side effects to occur provided that such higher dose levels are first divided into several smaller doses that are to be administered throughout the day. The compound may be administered alone or as an adjunct with other therapeutic regimens.

For purposes of oral administrations, tablets containing various excipients such as sodium citrate, calcium carbonate and dicalcium phosphate may be employed along with various disintegrants such as starch, alginic acid and certain complex silicates together with binding agents such as polyvinylpyrrolidone, sucrose, gelatin and acacia. Additionally, lubricating agents such as magnesium stearate, sodium lauryl sulfate and talc are often useful for tableting purposes. Solid compositions of a similar type may also be employed as fillers in soft and hard-filled gelatin capsules; preferred materials include lactose as well as high molecular weight polyethylene glycols. When aqueous suspensions and/or elixirs are desired for oral administration, the essential active ingredient therein may be combined with various sweetening or flavoring agents, coloring matter or dyes, and if desired, emulsifying and/or suspending agents as well, together with such diluents as water, ethanol, propylene glycol, glycerin and various combinations thereof.

For purposes of parenteral administration, solutions of a 16-aryl-13,14-dihydro-PGE$_2$ p-biphenyl ester in sesame or peanut oil or in aqueous propylene glycol may be employed.

EXAMPLE 1

Dimethyl 2-oxo-3-phenylpropylphosphonate

A solution of 6.2 g (50 mmoles) dimethyl methylphosphonate (Aldrich) in 125 ml dry tetrahydrofuran was cooled to $-78°$ in a dry nitrogen atmosphere. To the stirred phosphonate solution was added 21 ml of 2.37 M n-butyllithium in hexane solution (Alfa Inorganics, Inc.) dropwise over a period of 18 minutes at such a rate that the reaction temperature never rose above $-65°$. After an additional 5 minutes stirring at $-78°$, 7.5 g (50.0 mmole) methyl phenylacetate was added dropwise at a rate that kept the reaction temperature less than $-70°$ (20 minutes) After 3.5 hours at $-78°$, the reaction mixture was allowed to warm to ambient temperature, neutralized with 6 ml acetic acid and rotary evaporated (water aspirator) to a white gel. The gelatinous material was taken up in 75 ml water, the aqueous phase extracted with 100 ml portions of chloroform (3 x), the combined organic extracts were backwashed (50 ml H$_2$O), dried (MgSO$_4$), and concentrated in vacuo to a crude residue and distilled, b.p. 134°–5° (<0.1 mm) to give 3.5 g (29% dimethyl 2-oxo-3-phenylpropylphosphonate).

EXAMPLE 2

2-[3α-n-Phenylbenzoyloxy-5-a-hydroxy-2-β-(3-oxo-4-phenyl-trans-1-buten-1-yl) cyclopent-1α-yl]Acetic Acid, γ-lactone Dimethyl 2-oxo-3-phenylpropylphosphonate (3.4 g., 14.2 mmole) in 200 ml anhydrous ether was treated with 5.0 ml (12.5 mmole) 2.5 M n-butyllithium in n-hexane (Alfa Inorganics, Inc.) in a dry nitrogen atmosphere at room temperature. After 5 minutes stirring, an additional 400 ml of anhydrous ether was added followed by 3.85 g (11 mmole) 2-[3α-p-phenylbenzoyloxy-5α-hydroxy-2β-formylcyclopent -1α-yl]acetic acid, γ-lactone in one portion and 50 ml anhydrous ether. After 35 minutes the reaction mixture was quenched with 5 ml glacial acetic acid, washed with 100 ml saturated sodium bicarbonate solution (4 X), 100 ml water (2 X), 100 ml saturated brine, dried (MgSO$_4$) and evaporated to yield 2.908 g (57%) 2-[3α-p-phenylbenzoyloxy-5α-hydroxy-2β-(3-oxo-4-phenyl-trans-1-buten-1-yl)cyclopent-1α-yl]acetic acid, γ-lactone as a foam after column chromatography (silica gel, Baker, 60–200 mesh).

EXAMPLE 3

2-[3α-p-Phenylbenzoyloxy-5α-hydroxy-2β-(3α-hydroxy-4-phenyl-trans-1-buten-1-yl) cyclopent-1α-yl]acetic acid, γ-lactone and 2-[3α-n-Phenylbenzoyloxy-5α-hydroxy-2β-(3β-hydroxy-4-phenyl-trans-1-buten-1-yl)cyclopent-1α-yl]acetic acid, γ-lactone.

To a solution of 2908 mg (6.2 mmole) of 2-[3α-p-phenylbenzoyloxy-5α-hydroxy-2β-(3-oxo-4-phenyl-trans-1-buten-1-yl)cyclopent-1α-yl]acetic acid, γ-lactone in 30 ml dry 1,2-dimethoxyethane in a dry nitrogen atmosphere at ambient temperature was added dropwise 2.0 ml of a 1.0 M zinc borohydride solution in 1,2-dimethoxyethane. After stirring at 0° for 2 hours, a saturated sodium bitartrate solution was added dropwise until hydrogen evolution ceased. The reaction mixture was allowed to stir for 5 minutes at which time 250 ml dry methylene chloride was added. After drying (MgSO$_4$) and concentrating under vacuum, the resultant semisolid was purified by column chromatography on silica gel (Baker "Analyzed" Reagent 60–200 mesh) using ether as eluent. After elution of less polar impurities a fraction containing 658 mg 2-[3α-p-phenylbenzoyloxy-5α-hydroxy-2β-(3α-hydroxy-4-phenyl-trans-1-buten-1-yl)cyclopent-1α-yl]acetic acid, γ-lactone, and a 671 mg fraction of 2-[3α-p-phenylbenzoyloxy-5α-hydroxy-2β-(3β-hydroxy-4-phenyl-trans-1-buten-yl)cyclopent-1α-yl]acetic acid, γ-lactone were obtained.

EXAMPLE 4

2-[3α,5α-Dihydroxy-2β-(3α-hydroxy-4-phenyl-trans-1-buten-1-yl)cyclopent-1α-yl]acetic acid, γ-lactone A heterogeneous mixture of 658 mg (1.35 mmole) of 2-[3α-p-phenylbenzoyloxy-5α-hydroxy-2β-(3α-hydroxy-4-phenyl-trans-1-buten-1-yl)cyclopent-1α-yl]acetic acid, γ-lactone, 7.1 ml of absolute methanol and 188 mg of finely powdered anhydrous potassium carbonate was stirred at room temperature for 1 hour, then cooled to 0°. To the cooled solution was added 2.8 ml (2.8 mmole) of 1.0 N aqueous hydrochloric acid. After stirring at 0° for an additional 10 minutes, 5 ml of water was added with concomitant formation of methyl p-phenylbenzoate which was collected by filtration. The filtrate was saturated with solid sodium chloride, extracted with ethyl acetate (4 × 10 ml), the combined organic extracts washed with saturated sodium bicarbonate, dried and concentrated to give 381 mg of viscous, oily 2-[3α,5α-dihydroxy-2β-(3α-hydroxy-4-phenyl-trans-1-buten-1-yl)cyclopent-1α-yl]acetic acid, γ-lactone.

EXAMPLE 5

2-[5α-Hydroxy-3α-(tetrahydropyran-2-yloxy)-2β-(3α-[tetrahydropyran-2-yloxy]-4-phenyl-trans-1-buten-1yl)cyclopent-1α-yl]acetic acid, γ-lactone To a solution of 38 mg (1.33 mmole) 2-[3α,5α-dihydroxy-2β-(3α-hydroxy-4-phenyl-trans-1-buten-yl)cyclopent-1α-yl]acetic acid, γ-lactone in 5 ml anhydrous methylene chloride and 0.4 ml of 2,3-dihydropyran at 0° in a dry nitrogen atmosphere was added 5 mg p-toluenesulfonic acid monohydrate. After stirring for 15 minutes, the reaction mixture was combined with 100 ml ether, the ether solution washed with saturated sodium bicarbonate (1× 15 ml) then saturated brine (1× 15 ml), dried (MgSO$_4$) and concentrated to yield 615 mg (>100%) crude 2-[5α-hydroxy-3α-(tetrahydropyran-2-yloxy)-2β-(3α-[tetrahydropyran-2-yloxy]4-phenyl-trans-1-buten-1-yl)cyclopent-1α-yl]acetic acid, γ-lactone.

EXAMPLE 6

2-[5α-Hydroxy-3α(tetrahydropyran-2-yloxy)-2β-(3α-{tetrahydropyran-2-yloxy}4-phenylbut-1-yl)cyclopent-1α-yl]acetic acid, γ-lactone A stirred heterogeneous solution of 1.555 g (3.4 mmole) 2-[5α-hydroxy-3α(tetrahydropyran-2-yloxy)-2β-(3α-{tetrahydropyran-2-yloxy} -4-phenyl-trans-1-buten-1-yl)cyclopent-1αyl]acetic acid, γ-lactone and 300 mg 5% palladium on carbon in 35 ml absolute methanol was hydrogenated for 90 minutes. The reaction mixture was filtered through filter aid and concentrated in vacuo to yield 1.475 g of 2-[5α-hydroxy-3α-(tetrahydropyran-2-yloxy)-2β-3α-{tetrahydropryan-2-yloxy} -4-phenylbut-1-yl)cyclopentan-1α-yl]acetic acid, γ-lactone.

EXAMPLE 7

2-[5α-Hydroxy-3α-(tetrahydropyran-2-yloxy)-2β-(3α-{tetrahydropyran-2-yloxy} -4-phenylbut-1-yl)cyclopent-1α-yl]acetaldehyde, γ-hemacetal A solution of 1457 mg (3.2 mmole) 2-[5α-hydroxy-3α-(tetrahydropyran-2-yloxy)2β-(3α-{tetrahydropyran-2-yloxy} -4-phenylbut-1-yl)cyclopent-1α-yl]acetic acid, γ-lactone in 15 ml dry toluene was cooled to −78° in a dry nitrogen atmosphere. To this cooled solution was added 5.0 ml of 20% diisobutylaluminum hydride in n-hexane (Alfa Inorganics) dropwise at such a rate so that the internal temperature never rose above −65° (3 minutes). After an additional 30 minutes of stirring at −78°, anhydrous methanol was added until gas evolution ceased and the reaction mixture was allowed to warm to room temperature. The reaction mixture was combined with 150 ml ether, washed with 50% sodium potassium tartrate solution (1 × 50 ml), dried (Na$_2$SO$_4$), concentrated and chromatographed to yield 1200 mg (81.5%) 2-[5α-hydroxy-3-α-(tetrahydropyran-2-yloxy)-2β-(3α-{tetrahydropyran-2-yloxy} -4-phenylbut-1-yl)cyclopent-1α-yl]acetaldehyde, γ-hemiacetal.

EXAMPLE 8

9α-Hydroxy-11α,15α-bis-(tetrahydropyran-2-yloxy)-16-phenyl-cis-5-w-tetranor prostenoic acid To a solution of 5150 mg (11.6 mmole) 4-carbohydroxy-n-butyl) triphenylphosphonium bromide in a dry nitrogen atmosphere in 10.1 ml dry dimethyl sulfox was added 10.8 ml (21.1 mmole) of a 1.96 M solution of sodium methylsulfinylmethide in dimethyl sulfoxide. To this red ylide solution was added dropwise a solution of 1200 mg (2.6 mmole) 2-[5α-hydroxy-3α-(tetrahydropyran-2-yloxy)2β-(3α-{tetrahydropyran-2-yloxy } -4-phenyl-but-1-yl)cyclopent-1α-yl]acetaldehyde, γ-hemiacetal in 7.0 ml dry dimethyl sulfoxide over a period of 20 minutes. After an additional 2 hours stirring at room temperature, the reaction mixture was poured into ice water. The basic aqueous solution was acidified to pH 3 with 10% aqueous hydrochloric acid. The acidic solution was extracted with ethyl acetate (3 × 100 ml) and the combined organic extracts washed once with water (50 ml), dried (MgSO$_4$) and evaporated to a solid residue. This solid residue was triturated with ethyl acetate and filtered. The filtrate was purified by column chromatography on silica gel (Baker "Analyzed" Reagent 60–200 mesh) using ethyl acetate as eluent. After removal of impurities, 880 mg of 9α-hydroxy-11α,15α-bis-(tetrahydropyran-2-yloxy)-16-phenyl-cis-5-w-tetranor prostenoic acid was collected.

EXAMPLE 9

9-Oxo-11α,15α-bis-(tetrahydropyran-2-yloxy)-16-phenyl-cis-5-w-tetranor prostenoic acid To a solution cooled to -10° under nitrogen of 880 mg (1.68 mmole) 9α-hydroxy-11α,15α-bis-(tetrahydropyran-2-yloxy)-16-phenyl-cis-5-w-tetranor prostenoic acid in 15 ml reagent grade acetone was added dropwise 0.75 ml (2 mmole) of Jones' reagent. After 20 minutes at −10°, 0.75 ml 2-propanol was added and the reaction mixture was allowed to stir an additional 5 minutes at which time it was combined with 100 ml ethyl acetate, washed with water (3 × 25 ml), dried (MgSO$_4$) and concentrated to give 775 mg of 9-oxo-11α,15α-bis-(tetrahydropyran-2-yloxy)-16-phenyl-cis-5-w-tetranor prostenoic acid.

EXAMPLE 10

9-Oxo-11α,15α-dihydroxy-16-phenyl-cis-5-w-tetranor prostenoic acid

A solution of 772 mg 9-oxo-11α,15α-bis-(tetrahydropyran-2-yloxy)-16-phenylcis-5-w-tetranor prostenoic acid in 7.0 ml of a 65:35 mixture of glacial acetic acid:-water was stirred under nitrogen at 25° for 20 hours and then was concentrated by rotary evaporation. The resultant crude oil was purified by column chromatography on silica gel (Mallinckrodt CC-4 100–200 mesh) using ethyl acetate as effluent. After elution of less polar impurities, the oily 9-oxo-11α,15α-dihydroxy-16-phenyl-cis-5-w-tetranor prostenoic acid weighing 361 mg was collected.

EXAMPLE 11 p-Phenylphenol Ester of 16-phenyl-13,14-dihydro-w-tetranor-prostaglandin E$_2$

A solution of 120 mg (0.32 mmole) 16-phenyl-13,14-dihydroxy-w-tetranor-prostaglandin E$_2$, 545 mg (3.2 mmole) p-phenylphenol, 4.1 ml of 0.097 M dicyclohexylcarbodiimide in methylene chloride and 18 ml methylene chloride was stirred overnight at room temperature. Concentration in vacuo and column chromatography on silica gel (Baker, 60–200 mesh) yielded 75 mg (44%) of the p-phenylphenol ester of 16-phenyl-13,14-dihydro-w-tetranor -prostaglandin E$_2$, m.p. 90.5°–92°, after crystallization from ether-pentane. t,80

Analysis:

| | C | H |
|---|---|---|
| Calc'd for C$_{38}$H$_{38}$O$_5$: | 77.53 | 7.27 |
| Found: | 77.23 | 7.31 |

EXAMPLE 12

16-Aryl-13,14-dihydro-PGE$_2$ p-biphenyl esters were prepared by the procedures of Examples 1 to 11 to provide compounds where the aryl group is α- or β-furyl; α- or β-thienyl; α- or β-naphthyl; phenyl; 3,4-dimethoxy phenyl; 3,4-methylenedioxyphenyl; 3,4,5-trimethoxyphenyl and monosubstituted phenyl wherein said substituent is chlorine, bromine, fluorine, trifluoromethyl, phenyl, methyl and methoxy.

The appropriate aryl containing phosphonate is prepared by the method of Example 1 by using the appropriate aryl ester in place of methyl phenylacetate. The phosphonate thus prepared is used as the starting material of Example 2 in place of dimethyl-2-oxo-3-phenylpropylphosphonate.

EXAMPLE 13

Twelve beagle dogs per sex were separated into four groups of three males and three females each. All groups received gelatin capsules containing 16-phenyl13,14-dihydro-PGE$_2$ p-biphenyl ester and excipients consisting of polyvinylpyrrolidone, corn starch, lactose and talc 7 days a week for 35 days. Three groups received the prostaglandin at a dose level of 0.45, 0.25 and 0.1 mg/kg per day while the fourth group which served as the control received only the excipients at a level of 50 mg/kg per day.

There was no morphologic evidence of drug related tissue change in animals receiving dosage of the prostaglandin of 0.1 and 0.25 mg/kg per day. Of the 6 dogs receiving the highest dosage (0.45 mg/kg/day), 2 of 3 females and 1 of 3 males developed changes within the medullary canal of the femur characterized by marked bone deposition within that portion of the medullary canal normally filled with hematopoietic tissue and fat.

There was a drop in serum calcium of all the dogs receiving 0.45 mg/kg per day with the greatest drop occurring in those dogs in which increased bone deposition was observed.

There was an increase in the serum alkaline phosphatase levels of the three dogs in which increased bone deposition occurred.

EXAMPLE 14

Increased bone deposition may be produced by the method of Example 13 with other 16-aryl-13,14-dihydro-PGE$_2$ p-biphenyl esters where the aryl group is α-orβ-furyl; α- or β-thienyl; α- or β-naphthyl; dimethoxyphenyl; 3,4-methylenedioxyphenyl; 3,4,5-trimethoxyphenyl and monosubstituted phenyl wherein said substituent is chlorine, bromine, fluorine, trifluoromethyl, phenyl, methyl and methoxy.

What is claimed is:

1. A method for increasing bone deposition for the treatment of osteopenia which comprises administering to a subject afflicted with bone loss a bone deposition increasing amount of a 16-aryl-13,14-dihydro-PGE$_2$ p-biphenyl ester wherein the aryl group of said 13,14-dihydro-PGE$_2$ p-biphenyl ester is α- or β-furyl.

* * * * *